(12) United States Patent
Yang et al.

(10) Patent No.: US 12,011,580 B1
(45) Date of Patent: Jun. 18, 2024

(54) IMPELLER OF CARDIAC ASSIST DEVICE, AND CARDIAC ASSIST DEVICE

(71) Applicant: SHANGHAI PHIGINE MEDICAL CO. LTD, Shanghai (CN)

(72) Inventors: Yuncong Yang, Shanghai (CN); Xi Liu, Shanghai (CN); Haishan Wang, Shanghai (CN); Qifeng Yu, Shanghai (CN)

(73) Assignee: SHANGHAI PHIGINE MEDICAL CO. LTD, Shanghai (CN)

( * ) Notice: Subject to any disclaimer, the term of this patent is extended or adjusted under 35 U.S.C. 154(b) by 0 days.

(21) Appl. No.: 18/575,816

(22) PCT Filed: Jul. 7, 2022

(86) PCT No.: PCT/CN2022/104252
§ 371 (c)(1),
(2) Date: Dec. 29, 2023

(87) PCT Pub. No.: WO2023/280245
PCT Pub. Date: Jan. 12, 2023

(30) Foreign Application Priority Data

Jul. 7, 2021 (CN) .......................... 202110766881.8

(51) Int. Cl.
*A61M 60/408* (2021.01)
*A61M 60/122* (2021.01)
(Continued)

(52) U.S. Cl.
CPC ........ *A61M 60/216* (2021.01); *A61M 60/122* (2021.01); *A61M 60/438* (2021.01); *A61M 60/806* (2021.01)

(58) Field of Classification Search
None
See application file for complete search history.

(56) References Cited

U.S. PATENT DOCUMENTS

| 2011/0152599 A1 | 6/2011 | Bokeriya et al. |
| 2013/0303830 A1 | 11/2013 | Zeng et al. |
| 2014/0341726 A1 | 11/2014 | Wu et al. |

FOREIGN PATENT DOCUMENTS

| CN | 201539437 U | 8/2010 |
| CN | 101822854 A | 9/2010 |

(Continued)

*Primary Examiner* — Jon Eric C Morales
(74) *Attorney, Agent, or Firm* — THE SUN IP LAW (57) ABSTRACT

The present disclosure discloses an impeller of a cardiac assist device, and the cardiac assist device. The impeller of the cardiac assist device includes an impeller shaft and a plurality of blades; a shape of the plurality of blades is set such that: blade cascades of the plurality of blades are of arc lines that recess towards a same side, and the blade cascade is a planar unfolding shape of an intersection line where a cylindrical surface intersects with the blade. In the present disclosure, a traditional wing-shaped blade cascade is changed, the blade cascades are of arc lines that recess towards the same side, this design enables blood to pass through the impeller at a smaller inflow angle and a greater outflow angle, the smaller inflow angle may generate a greater lift, so that the impeller obtains a greater output power, and meanwhile, a rotational flow can be prevented from being generated at an inflow port, such that the blood stably flows into the impeller. The greater outflow angle can convert the rotation energy of the blood at an outflow port into an axial kinetic energy, thereby obtaining a greater axial speed, and improving the efficiency of the impeller.

18 Claims, 5 Drawing Sheets

(51) Int. Cl.
*A61M 60/216* (2021.01)
*A61M 60/221* (2021.01)
*A61M 60/237* (2021.01)
*A61M 60/438* (2021.01)
*A61M 60/806* (2021.01)

(56) References Cited

FOREIGN PATENT DOCUMENTS

| | | |
|---|---|---|
| CN | 101822855 A | 9/2010 |
| CN | 102587998 A | 7/2012 |
| CN | 105498002 A | 4/2016 |
| CN | 106039442 A | 10/2016 |
| CN | 206443963 U | 8/2017 |
| CN | 112807564 A | 5/2021 |

IMPELLER OF CARDIAC ASSIST DEVICE, AND CARDIAC ASSIST DEVICE

CROSS-REFERENCE TO RELATED APPLICATION

The disclosure claims priority to Chinese Patent Application No. 202110766881.8, filed on Jul. 7, 2021 and entitled "Impeller of Cardiac Assist Device, and Cardiac Assist Device".

TECHNICAL FIELD

The present disclosure relates to the technical field of medical instruments, and in particular, to an impeller of a cardiac assist device, and the cardiac assist device.

BACKGROUND

A percutaneous ventricular assist device is a more novel product compared to a traditional ventricular assist device or a cardiac blood pump, and the main advantage of the percutaneous ventricular assist device is that it can be implanted into a heart in a minimally invasive manner such as femoral artery puncture or incision without being implanted through a thoracotomy, thereby greatly reducing the surgical risks. This advantage enables the percutaneous ventricular assist device to be used for maintaining the vital signs of a severe heart failure patient, or assisting in the treatment in high-risk PCI surgery, so as to reduce the surgical risks. However, since the percutaneous ventricular assist device needs to be implanted into the left ventricle through the femoral artery, the size of the percutaneous ventricular assist device needs to be smaller than that of the traditional ventricular assist device, so as to meet the requirements of smoothly passing through the femoral artery and the aorta. Generally, the outer diameter of the percutaneous ventricular assist device needs to be less than 21 Fr/7 mm. An axial flow pump serves as a core assembly of ventricular assist, and a built-in impeller can play a function of pumping the blood from the left ventricle into the aorta at a high rotating speed, so that the effect of the impeller is crucial. According to an intracardiac pumping device disclosed in the patent document U.S. Pat. No. 9,872,948B2, the impeller is located in a pump box having the same outer diameter as the product, so that the size of the impeller is less than the outer diameter of the product. Typically, the diameter of the impeller is less than 6 mm. However, the existing impeller cannot simultaneously meet the requirement of a miniature size and achieve a sufficient flow rate to help the ventricular assist device to maintain the vital signs of the patient.

In view of this, it is urgent to improve the impeller of the existing cardiac assist device, so as to not only meet the requirement of the miniature size, but also achieve a sufficient flow rate to help the ventricular assist device to maintain the vital signs of the patient.

SUMMARY

The present disclosure discloses an impeller of a cardiac assist device, and the cardiac assist device, which is used for solving the problem in the prior art that the impeller of the cardiac assist device cannot simultaneously meet the requirement of a miniature size and achieve a sufficient flow rate to help a ventricular assist device to maintain the vital signs of a patient.

In order to solve the above problem, the present disclosure utilizes the following technical solutions:

Provided is an impeller of a cardiac assist device, including an impeller shaft and a plurality of blades; a shape of the plurality of blades is set such that: blade cascades of the plurality of blades are of arc lines that recess towards a same side, and each of the blade cascades conforms to a function:

$$\begin{cases} r = r^* \\ \theta = 180t \\ z = a*\tan(bt) \end{cases}$$

wherein, $r^*$ is a radius of a cylindrical surface where the function is located, $\theta$ is an angle dependent variable, $z$ is an axial dependent variable, $t$ is an independent variable, and $0 \leq t \leq 1$, and $a$ and $b$ are coefficients; and the blade cascade is a planar unfolding shape of an intersection line where the cylindrical surface intersects with the blade.

In some embodiments, a rotating speed of the impeller and a radius of the impeller both have an arccosine relationship with the coefficient $b$.

In some embodiments, the rotating speed of the impeller is 30000-90000 RPM.

In some embodiments, a value range of the coefficient $b$ is 20 to 78.

In some embodiments, the rotating speed of the impeller is 35000 RPM.

In some embodiments, a value of the coefficient $b$ is 60.

In some embodiments, the coefficient $a$ is positively correlated with a flow rate of the impeller.

In some embodiments, the flow rate of the impeller is 4 L/min.

In some embodiments, a value of the coefficient $a$ is 3.5.

In some embodiments, an outer diameter of the impeller is 5 mm.

In some embodiments, a diameter of a middle portion of the impeller shaft is 2.5 mm, and a hub ratio is 0.5.

In some embodiments, a functional equation of the blade cascade is:

$$\begin{cases} r = 2.5 \\ \theta = 180t \\ z = 3.5*\tan(60t) \end{cases}.$$

In some embodiments, an axial length of the blade and a height of the blade cascade are equal and do not exceed 6 mm.

In some embodiments, inflow ends and outflow ends of the blade cascades are respectively connected through a first straight line and a second straight line, an included angle between the first straight line and a first tangent line of a first arc line is a first angle, an included angle between the second straight line and a second tangent line of a second arc line is a second angle, the first angle ranges from 10° to 20°, and the second angle ranges from 40° to 50°.

In some embodiments, there are two blades.

In some embodiments, an inflow end of the impeller shaft is a cone, a middle portion of the impeller shaft is a cylinder, and an outflow end of the impeller shaft is an inwardly recessed arc surface.

The present disclosure further provides a cardiac assist device, including the impeller in any one of the above embodiments, and further including:

a motor, connected with an outflow end of the impeller;
a sleeve, disposed on a periphery of the impeller and the motor; and
a cannula, connected with an inflow end of the sleeve;
wherein an end of the cannula away from the impeller is connected with an inflow chamber, and an end of the cannula close to the motor is connected with an outflow chamber.

In some embodiments, an arc line of a tail of the impeller has continuity with an arc line of a front end of the motor.

The technical solutions utilized in the present disclosure can achieve the following beneficial effects:

A traditional wing-shaped blade cascade is changed, the blade cascades are of the arc lines that recess towards the same side, this design enables blood to pass through the impeller at a smaller inflow angle and a greater outflow angle, the smaller inflow angle may generate a greater lift, so that the impeller obtains a greater output power, and meanwhile, a rotational flow can be prevented from being generated at an inflow port, such that the blood stably flows into the impeller. The greater outflow angle can convert the rotation energy of the blood at an outflow port into an axial kinetic energy, thereby obtaining a greater axial speed, and improving the efficiency of the impeller.

BRIEF DESCRIPTION OF THE DRAWINGS

In order to more clearly illustrate the technical solutions of the embodiments of the present disclosure, the drawings that need to be used in the description of the embodiments are briefly described below, the drawings constitute a part of the present disclosure, and schematic embodiments of the present disclosure and the description thereof explain the present disclosure, and do not constitute an improper limitation on the present disclosure. In the drawings.

Specifically, the following reference signs are included: impeller—10; motor—20; blade—11; impeller shaft—12; blade cascade—13; inflow chamber—30; cannula—40; sleeve—50; first straight line—L1; second straight line—L2; first arc line—A1; second arc line—A2.

DETAILED DESCRIPTION OF THE EMBODIMENTS

In order to make the objectives, technical solutions and advantages of the present disclosure more clearly understood, a clear and complete description of technical solutions of the present disclosure will be given below, in combination with specific embodiments of the present disclosure and corresponding drawings. Apparently, the embodiments described below are merely a part, but not all, of the embodiments of the present disclosure. All of other embodiments, obtained by those ordinary skilled in the art based on the embodiments in the present disclosure without any creative effort, fall into the protection scope of the present disclosure.

Embodiment 1

Figure 1:
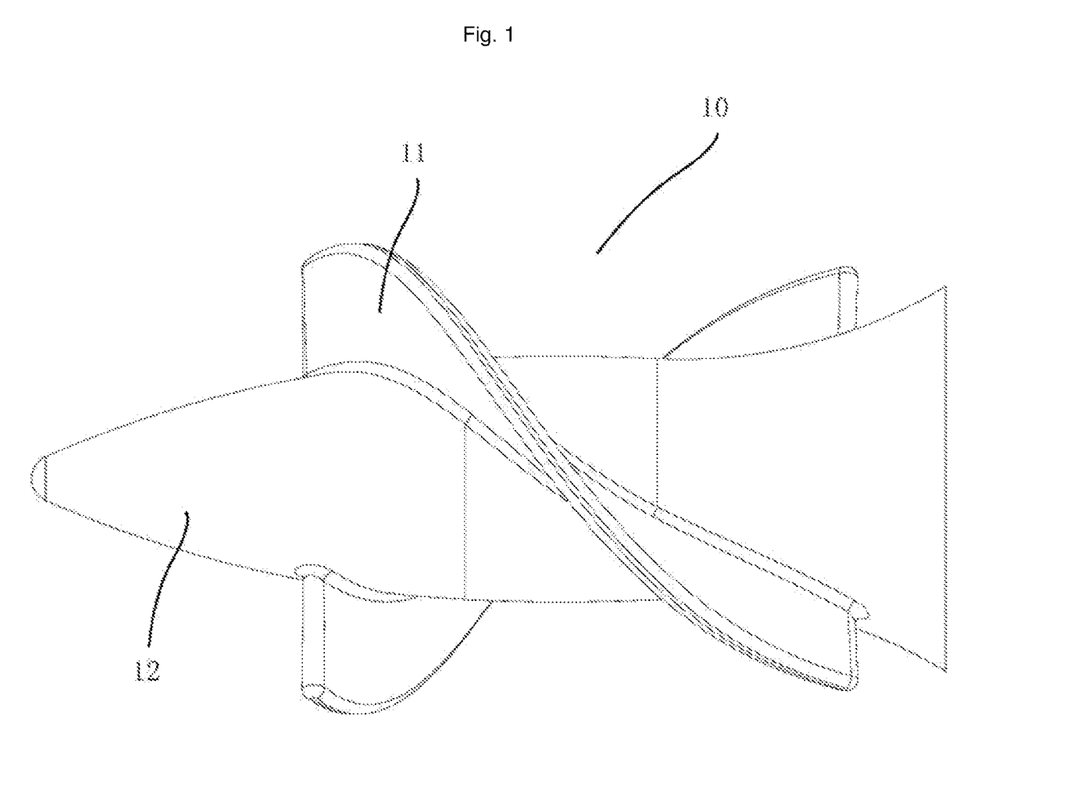
FIG. 1 is a side view of an impeller of a cardiac assist device disclosed in Embodiment 1 of the present disclosure.
Figure 2:
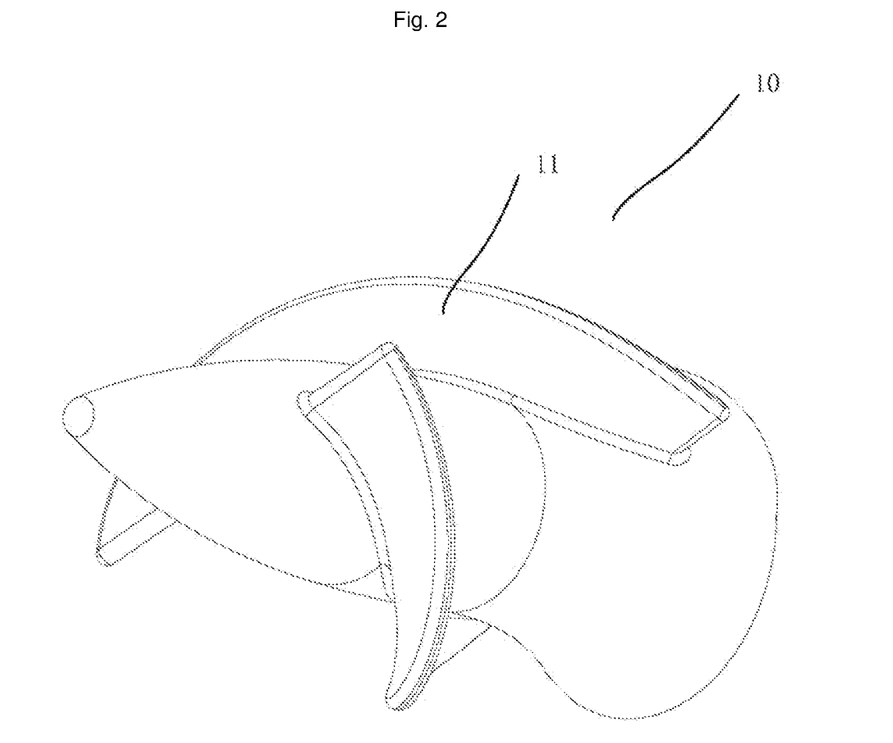
FIG. 2 is a schematic diagram of another angle of view of the impeller of the cardiac assist device disclosed in Embodiment 1 of the present disclosure.
Figure 3:
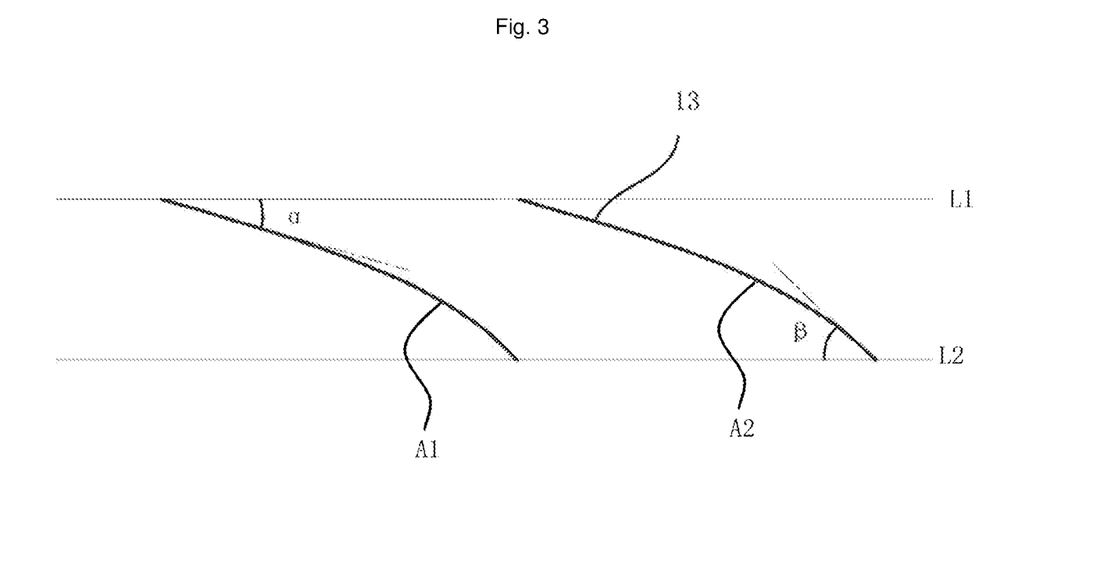
FIG. 3 is a schematic diagram of a blade cascade of the cardiac assist device disclosed in Embodiment 1 of the present disclosure.

As shown in FIGS. 1-3, an impeller of a cardiac assist device provided in the present disclosure includes an impeller shaft 12 and a plurality of blades 11;

a shape of the plurality of blades is set such that: blade cascades 13 of the plurality of blades 11 are of arc lines that recess towards a same side, and each of the blade cascades 13 conforms to a function:

$$\begin{cases} r = r^* \\ \theta = 180t \\ z = a*\tan(bt) \end{cases}$$

in the formula, r* is a radius of a cylindrical surface where the function is located, θ is an angle dependent variable, z is an axial dependent variable, t is an independent variable, and 0≤t≤1, and a and b are coefficients; and the blade cascade 13 is a planar unfolding shape of an intersection line where the cylindrical surface intersects with the blade 11.

In the present disclosure, a traditional wing-shaped blade cascade is changed, the blade cascades 13 are of the arc lines that recess towards the same side, this design enables blood to pass through the impeller 10 at a smaller inflow angle and a greater outflow angle, the smaller inflow angle may generate a greater lift, so that the impeller 10 obtains a greater output power, and meanwhile, a rotational flow can be prevented from being generated at an inflow port, such that the blood stably flows into the impeller 10. The greater outflow angle can convert the rotation energy of the blood at an outflow port into an axial kinetic energy, thereby obtaining a greater axial speed, and improving the efficiency of the impeller 10.

In the present embodiment, t represents an abstract time concept, when t=0, the axial dependent variable z is 0, which denotes a starting position of the blade 11, and when t=1, it indicates that the time passing through the blade 11 is a unit 1, and at this time, the value of the axial dependent variable z is the axial length of the blade 11.

Figure 4:
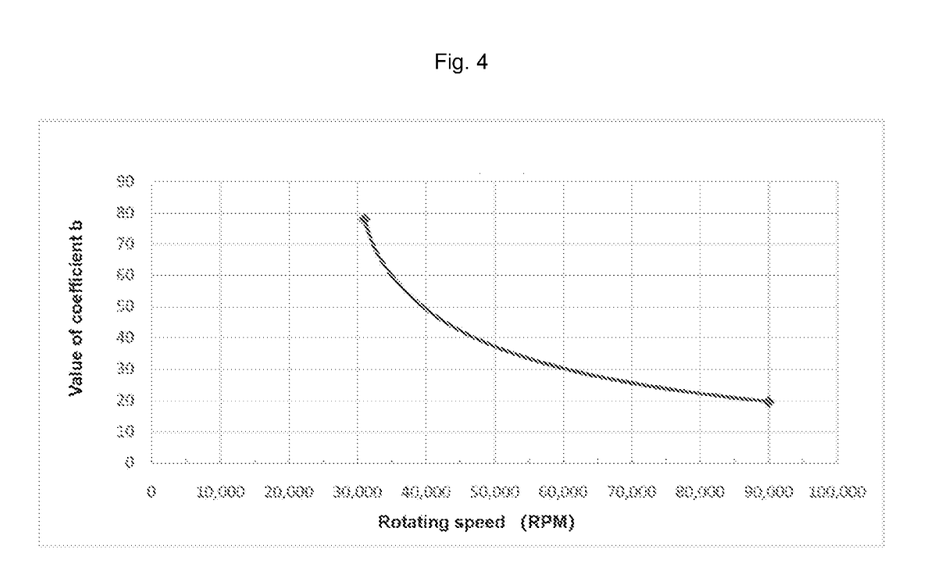
FIG. 4 is a diagram showing a relationship curve between a rotating speed and a coefficient b of the impeller disclosed in Embodiment 1 of the present disclosure.

As shown in FIG. 4, by establishing a mathematical model, the coefficient b is mainly related to a rotating speed of the impeller 10 and a radius of the impeller 10, and there is an arccosine relationship. When the rotating speed of the impeller 10 is within a value range of 30000-90000 RPM, the coefficient b is a real value, and the corresponding value range is 20-78.

In the present embodiment, preferably, the rotating speed of the impeller is 35000 RPM. The value of the coefficient b is 60.

Figure 5:
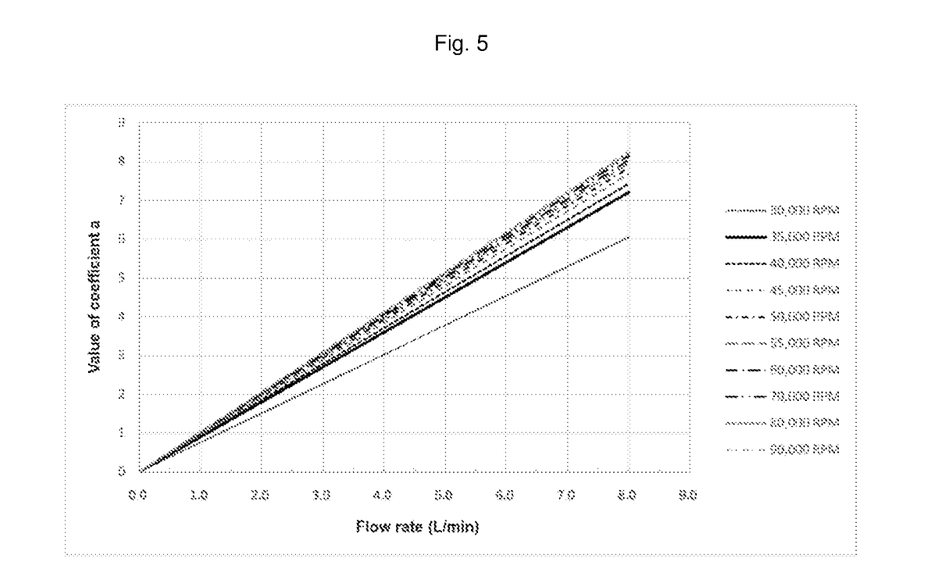
FIG. 5 is a diagram showing a linear relationship between a flow rate and a coefficient a of the impeller disclosed in Embodiment 1 of the present disclosure.

As shown in FIG. 5, the coefficient a is positively correlated with a flow rate of the impeller 10. Therefore, after the value of the coefficient b is calculated at a fixed rotating speed, a mathematical relationship between the coefficient a and the flow rate of the impeller 10 may be obtained. Under the value of a specific rotating speed and the corresponding coefficient b of the impeller 10, the coefficient a has a mathematical linear relationship with the flow rate of the impeller 10. In the present embodiment, preferably, the flow rate of the impeller is 4 L/min, and the value of the coefficient a is about 3.5.

In the present embodiment, preferably, an outer diameter of the impeller 10 is 5 mm. A diameter of a middle portion of the impeller shaft 12 is 2.5 mm, and a hub ratio is 0.5.

After the coefficient a and the coefficient b are substituted with the preferred values of the present embodiment, the functional equation of the blade cascade 13 is:

$$\begin{cases} r = 2.5 \\ \theta = 180t \\ z = 3.5 * \tan(60t) \end{cases}$$

when t=1, the value of z is the axial length of the blade 11 and is also the height of the blade cascade 13, and in present embodiment, preferably, the value of z is about 6 mm.

Inflow ends and outflow ends of the blade cascades 13 are respectively connected through a first straight line L1 and a second straight line L2, an included angle between the first straight line L1 and a first tangent line of a first arc line A1 is α, an included angle between the second straight line L2 and a second tangent line of a second arc line A2 is β, α ranges from 10° to 20°, and β ranges from 40° to 50°.

In the present embodiment, preferably, there are two blades 11.

In the present embodiment, preferably, an inflow end of the impeller shaft 12 is a cone, a middle portion of the impeller shaft 12 is a cylinder, and an outflow end of the impeller shaft 12 is an inwardly recessed arc surface; and since the inflow end of the impeller shaft 12 is the cone, the blood flow can smoothly flow into the impeller 10, and since the side surface of the outflow end is the inwardly recessed arc surface, the blood flow can pass through an arc line.

In the present embodiment, preferably, a projection of an outer edge of the blade 11 at an axial center of the impeller shaft 12 is always perpendicular to an axis of the impeller shaft 12.

Embodiment 2

Figure 6:
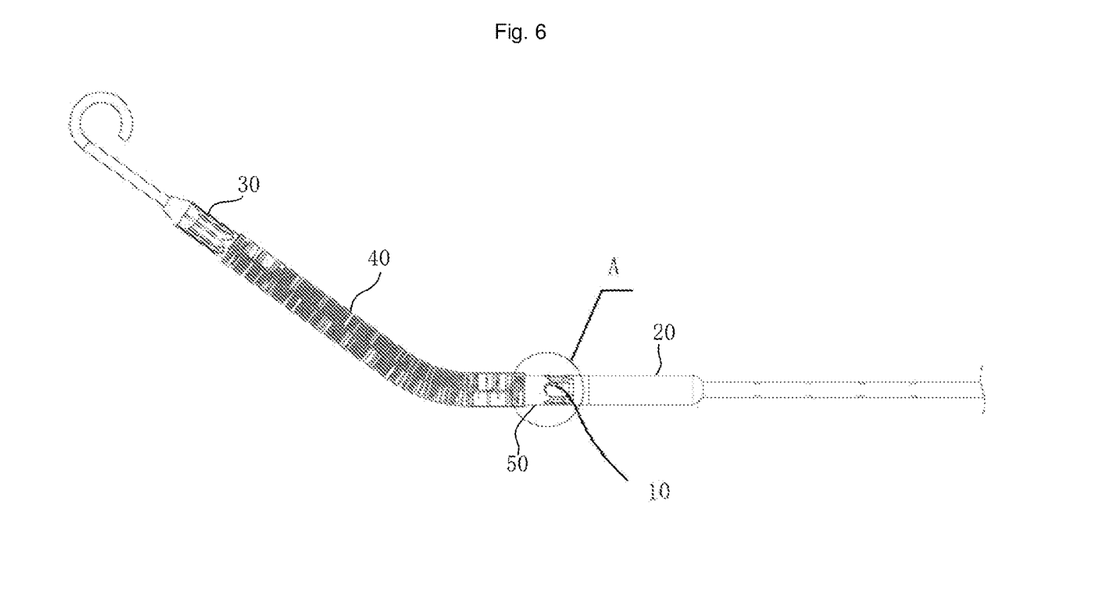
FIG. 6 is a schematic diagram of an overall structure of a cardiac assist device disclosed in Embodiment 2 of the present disclosure.
Figure 7:
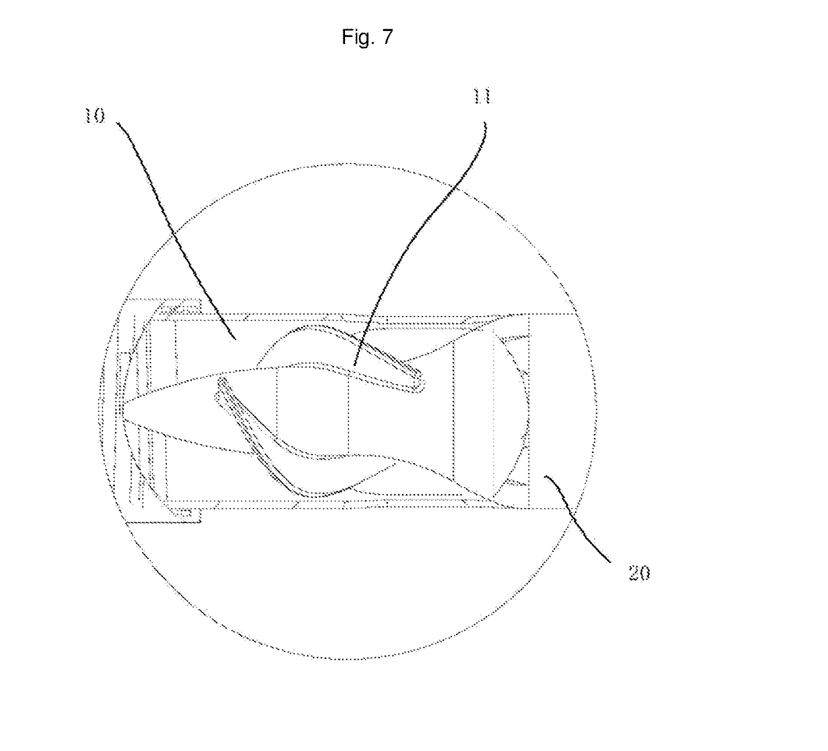
FIG. 7 is an enlarged view of an internal structure at a location A in FIG. 4.
Figure 8:
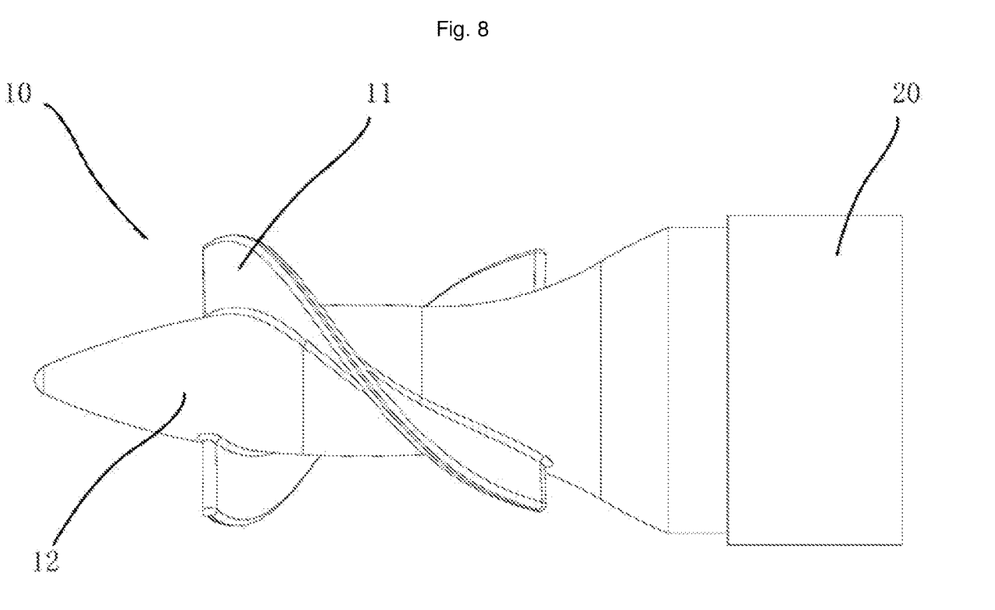
FIG. 8 is a schematic diagram of a connection between an impeller and a motor of the cardiac assist device disclosed in Embodiment 2 of the present disclosure.

As shown in FIGS. 6-8, the present disclosure further discloses a cardiac assist device, including the impeller 10 in Embodiment 1, and further including:
a motor 20, connected with an outflow end of the impeller 10; a sleeve 50, disposed on a periphery of the impeller 10 and the motor 20; and a cannula 40, connected with an inflow end of the sleeve 50; wherein an end of the cannula 40 away from the impeller 10 is connected with an inflow chamber 30, and an end of the cannula 40 close to the motor 20 is connected with an outflow chamber (the sleeve 50 serves as the outflow chamber).

Preferably, an arc line of a tail of the impeller 10 has continuity with an arc line of a front end of the motor 20. Therefore, it is ensured that the blood flow passes through an arc line and can flow on the surface of the motor 20 after flowing out of the impeller 10, therefore the surface of the motor 20 is cooled by the flow of the blood.

In the present disclosure, the traditional wing-shaped blade cascade is changed, the blade cascades are of the arc lines that recess towards the same side, this design enables blood to pass through the impeller at a smaller inflow angle and a greater outflow angle, the smaller inflow angle may generate a greater lift, so that the impeller obtains a greater output power, and meanwhile, a rotational flow can be prevented from being generated at an inflow port, such that the blood stably flows into the impeller. The greater outflow angle can convert the rotation energy of the blood at an outflow port into an axial kinetic energy, thereby obtaining a greater axial speed, and improving the efficiency of the impeller.

The embodiments of the present disclosure are described above with reference to the drawings, but the present disclosure is not limited to the specific embodiments described above, and the specific embodiments described above are merely illustrative rather than restrictive, and those ordinary skilled in the art can also make many forms without departing from the spirit of the present disclosure and the protection scope of the claims, and all these forms fall within the protection of the present disclosure.

What is claimed is:

1. An impeller of a cardiac assist device, comprising an impeller shaft and a plurality of blades;
   a shape of the plurality of blades is set such that: blade cascades of the plurality of blades are of arc lines that recess towards a same side, and each of the blade cascades conforms to a function:

$$\begin{cases} r = r^* \\ \theta = 180t \\ z = a * \tan(bt) \end{cases}$$

wherein, r* is a radius of a cylindrical surface where the function is located, θ is an angle dependent variable, z is an axial dependent variable, t is an independent variable, and 0≤t≤1, and a and b are coefficients; and the blade cascade is a planar unfolding shape of an intersection line where the cylindrical surface intersects with the blade.

2. The impeller of the cardiac assist device according to claim 1, wherein a rotating speed of the impeller and a radius of the impeller both have an arccosine relationship with the coefficient b.

3. The impeller of the cardiac assist device according to claim 2, wherein the rotating speed of the impeller is 30000-90000 RPM.

4. The impeller of the cardiac assist device according to claim 3, wherein a value range of the coefficient b is 20 to 78.

5. The impeller of the cardiac assist device according to claim 2, wherein the rotating speed of the impeller is 35000 RPM.

6. The impeller of the cardiac assist device according to claim 5, wherein a value of the coefficient b is 60.

7. The impeller of the cardiac assist device according to claim 6, wherein the coefficient a is positively correlated with a flow rate of the impeller.

8. The impeller of the cardiac assist device according to claim 7, wherein the flow rate of the impeller is 4 L/min.

9. The impeller of the cardiac assist device according to claim 8, wherein a value of the coefficient a is 3.5.

10. The impeller of the cardiac assist device according to claim 9, wherein an outer diameter of the impeller is 5 mm.

11. The impeller of the cardiac assist device according to claim 10, wherein a diameter of a middle portion of the impeller shaft is 2.5 mm, and a hub ratio is 0.5.

12. The impeller of the cardiac assist device according to claim 11, wherein a functional equation of the blade cascade is:

$$\begin{cases} r = 2.5 \\ \theta = 180t \\ z = 3.5 * \tan(60t) \end{cases}.$$

13. The impeller of the cardiac assist device according to claim 12, wherein an axial length of the blade and a height of the blade cascade are equal and do not exceed 6 mm.

14. The impeller of the cardiac assist device according to claim 12, wherein inflow ends and outflow ends of the blade cascades are respectively connected through a first straight line and a second straight line, an included angle between the first straight line and a first tangent line of a first arc line is a first angle, an included angle between the second straight line and a second tangent line of a second arc line is a second angle, the first angle ranges from 10° to 20°, and the second angle ranges from 40° to 50°.

15. The impeller of the cardiac assist device according to claim 12, wherein there are two blades.

16. The impeller of the cardiac assist device according to claim 1, wherein an inflow end of the impeller shaft is a cone, a middle portion of the impeller shaft is a cylinder, and an outflow end of the impeller shaft is an inwardly recessed arc surface.

17. A cardiac assist device, comprising the impeller according to claim 1, and further comprising:
  a motor, connected with an outflow end of the impeller;
  a sleeve, disposed on a periphery of the impeller and the motor; and
  a cannula, connected with an inflow end of the sleeve;
  wherein an end of the cannula away from the impeller is connected with an inflow chamber, and an end of the cannula close to the motor is connected with an outflow chamber.

18. The cardiac assist device according to claim 17, wherein an arc line of a tail of the impeller has continuity with an arc line of a front end of the motor.

\* \* \* \* \*